(12) United States Patent
Lindner et al.

(10) Patent No.: US 7,744,650 B2
(45) Date of Patent: Jun. 29, 2010

(54) VERTEBRAL BODY REPLACEMENT IMPLANT

(75) Inventors: Stephan Lindner, Tuttlingen (DE); Jens Beger, Tuttlingen (DE); Sven Diehl, Zweibruecken (DE); Allan Maas, Constance (DE)

(73) Assignee: Aesculap AG, Tuttlingen (DE)

( * ) Notice: Subject to any disclaimer, the term of this patent is extended or adjusted under 35 U.S.C. 154(b) by 963 days.

(21) Appl. No.: 11/436,899

(22) Filed: May 17, 2006

(65) Prior Publication Data

US 2006/0293755 A1 Dec. 28, 2006

(30) Foreign Application Priority Data

May 19, 2005 (DE) .................. 10 2005 022 921

(51) Int. Cl.
*A61F 2/44* (2006.01)

(52) U.S. Cl. .................. 623/17.14; 623/17.15; 606/90

(58) Field of Classification Search ........... 606/105, 606/257, 258; 623/17.11, 17.12, 17.13, 17.14, 623/17.15, 17.16

See application file for complete search history.

(56) References Cited

U.S. PATENT DOCUMENTS

| 4,759,766 | A | | 7/1988 | Buettner-Janz et al. |
| 5,062,850 | A | * | 11/1991 | MacMillan et al. ....... 623/17.11 |
| 5,480,442 | A | * | 1/1996 | Bertagnoli ............... 623/17.14 |
| 5,961,516 | A | * | 10/1999 | Graf .......................... 606/256 |
| 6,221,111 | B1 | * | 4/2001 | Piveteau et al. .......... 623/23.57 |
| 6,299,644 | B1 | * | 10/2001 | Vanderschot ............. 623/17.15 |
| 6,344,057 | B1 | * | 2/2002 | Rabbe et al. ............. 623/17.11 |
| 7,351,261 | B2 | * | 4/2008 | Casey ....................... 623/17.13 |
| 7,563,281 | B2 | * | 7/2009 | Sears et al. ............... 623/17.11 |
| 2003/0045877 | A1 | * | 3/2003 | Yeh .............................. 606/61 |
| 2004/0117021 | A1 | | 6/2004 | Biedermann et al. |
| 2005/0004572 | A1 | | 1/2005 | Biedermann et al. |
| 2005/0060036 | A1 | | 3/2005 | Schultz et al. |
| 2005/0090898 | A1 | * | 4/2005 | Berry et al. .............. 623/17.11 |
| 2006/0015183 | A1 | * | 1/2006 | Gilbert et al. ............. 623/17.11 |

FOREIGN PATENT DOCUMENTS

| DE | 239 523 | 4/1993 |
| DE | 203 11 400 | 11/2003 |
| DE | 102 42 329 | 3/2005 |
| EP | 1 346 709 | 9/2003 |
| EP | 1 398 008 | 3/2004 |
| EP | 1 417 940 | 5/2004 |
| EP | 1 135 076 | 11/2005 |

\* cited by examiner

*Primary Examiner*—Eduardo C Robert
*Assistant Examiner*—Lynnsy Schneider
(74) *Attorney, Agent, or Firm*—Lipsitz & McAllister, LLC

(57) ABSTRACT

A vertebral body replacement implant having an upper and a lower support plate and two load-bearing elements, the mutual spacing of which is adjustable and of which at least one is connected in an articulated manner to a support plate, the load-bearing element in the region of the articulated connection to the support plate having a bearing projection with a spherical lateral support surface having a complimentary design to the contact surface of the support plate or a bearing part connected thereto, the contact surface extending in peripheral direction at least over 180°, the support plate or the bearing part is mounted on the bearing projection pivotably about a pivotal axis that extends parallel to the support plate, and a releasable clamping device that clamps the bearing projection and the support plate or the bearing part in the contact region of the lateral surface and/or of the contact surface against one another.

31 Claims, 6 Drawing Sheets

VERTEBRAL BODY REPLACEMENT IMPLANT

The present disclosure relates to the subject matter disclosed in German application number 10 2005 022 921.2 of May 19, 2005, which is incorporated herein by reference in its entirety and for all purposes.

BACKGROUND OF THE INVENTION

The invention relates to a vertebral body replacement implant having an upper and a lower support plate for positioning against end faces of vertebral bodies and having two load-bearing elements, the mutual spacing of which is adjustable and of which at least one is connected in an articulated manner to a support plate.

Such a vertebral body replacement implant is known for example from DE 20311400 U1, in which the support plates are designed to be pivotable about an axis extending transversely of the direction of displacement of the implant so that the implant, as it is introduced into the body, has as low a cross section as possible, thereby allowing introduction even through small accesses.

SUMMARY OF THE INVENTION

Proceeding from this background art, the underlying object of the invention is to design a vertebral body replacement implant of said type in a way that allows, on the one hand, easy use of support plates of differing geometry and, on the other hand, an optimum fastening of the support plates to the implant so that even large tilting moments, such as arise for example when the support plates are loaded at the edge, may be reliably taken up by the implant.

In a vertebral body replacement implant of the initially described type, this object is achieved according to the invention in that the load-bearing element in the region of the articulated connection to the support plate has a bearing projection with a spherical lateral surface, in that the support plate or a bearing part connected thereto rests with a contact surface, which is of a complementary design to the spherical support surface, against the lateral surface over an angular range that extends in peripheral direction at least over 180°, in that the support plate or the bearing part is mounted on the bearing projection pivotably about a pivotal axis extending parallel to the support plate, and in that a clamping device that clamps the bearing projection, on the one hand, and the support plate or the bearing part in the contact region of the lateral surface and/or of the contact surface, on the other hand, against one another is provided, by means of which in a clamping position the bearing projection and the support plate and the bearing part are clamped non-pivotably relative to one another and in a release position are released so that they are freely pivotable relative to one another about the pivotal axis.

The guidance of the support plate or the bearing part on the bearing projection by means of spherical bearing- and contact surfaces leads to particularly reliable guidance of the support plate on the load-bearing element and it is moreover possible in this region by means of a clamping operation to achieve a particularly reliable fixing of the support plate relative to the load-bearing element. With this arrangement, it is easily possible to exchange the support plate, this merely involving slipping the support plate, or the support plate together with the bearing part, from above onto the bearing projection, then effecting provisional fixing simply by means of a component that defines the pivotal axis and permanent fixing by means of the clamping device.

To insert the implant between two vertebrae, the support plates are freely pivotable about the pivotal axis so that their position may be adapted to the desired position of the vertebral bodies and, once this position has been reached, it is permanently maintained by fixing of the clamping device.

A particularly advantageous development arises when the support plate is of a U-shaped design having two substantially parallel limbs connected by a transverse web, when moreover the limbs are disposed on either side of the spherical bearing projection, when the pivotal axis extends parallel to the transverse web, and when the clamping device in the clamping position clamps the two limbs towards one another at their free ends remote from the transverse web. In the clamping position, therefore, the two limbs clamp the spherical bearing projection in between them, the limbs being held together at one end by the transverse web, at the other end by the clamping device.

The clamping device may be in particular a clamping screw that extends parallel to the pivotal axis and rests against the free ends of the limbs.

It is advantageous when the longitudinal axis of the clamping screw and the pivotal axis define a bearing plane that extends at a spacing from, and substantially parallel to, a supporting surface of the support plate that is positionable against a vertebral body.

In a preferred form of construction, it is provided that the pivotal axis is defined by a bearing shaft that may be screwed into the bearing projection. This admittedly means that the support plate prior to actuation of the clamping device is connected by a ball joint to the bearing body but the degrees of freedom of the ball joint are limited by the screwed-in bearing shaft, so that only pivoting about one pivotal axis is possible. In said case, however, the two bodies pivoted towards one another are guided by the spherical contact surfaces, i.e. not all bearing forces need be transmitted via the bearing shaft, which is used merely to limit the degrees of freedom of motion. After actuation of the clamping device, the forces are transmitted between support plate, on the one hand, and load-bearing element, on the other hand, substantially via the spherical contact surfaces that are clamped against one another and not via the bearing shaft, which may therefore be dimensioned correspondingly small.

The spherical contact surface may be formed directly on the support plate itself, which then rests directly against the bearing body.

In another embodiment, between support plate and spherical bearing body a special bearing part is inserted, which according to a preferred form of construction takes the form of a bearing ring that has a continuous dividing slot along its circumference. By virtue of this dividing slot it is possible to compress the bearing ring, i.e. the clamping device may press the bearing ring in a clamping manner against the outside of the spherical bearing body, thereby effecting reliable fixing.

The bearing ring may be disposed in a recess of the support plate and lie with its outer side against the inner wall of the recess. In particular, this recess will be a cylindrical recess, while the bearing ring has a corresponding cylindrical outer side, so that the bearing ring may easily be inserted into and removed from the recess of the support plate. This facilitates the exchange of a support plate, which may namely be removed from a load-bearing element with bearing ring and replaced by another one very easily.

In a modified form of construction, the outer side of the bearing ring may also be of a crowned design and then rests against an inner wall of the recess that is of a complementary design, so that the bearing ring, whilst it may easily be snapped elastically onto the bearing body, after being firmly clamped may by virtue of the crowned construction also take up axial forces and axial moments and hence remove load from the bearing shaft.

The recess preferably forms a central opening in the support plate.

It is advantageous when the support plate in the region of the transverse web is of an elastically deformable design. This allows the limbs of the support plate to be clamped towards one another at their free ends by means of the clamping device. During this clamping of the limbs, the transverse web is slightly elastically distorted.

This elastic deformability may be assisted for example by the support plate having a lower thickness in the region of the transverse web than in the region of the limbs.

The support plate might rest with its limbs and its transverse web directly against the end faces of the vertebral bodies. In such a case, it is however not absolutely guaranteed that the support plate will rest against the vertebral bodies in the regions that have a particularly high strength and are therefore particularly capable of bearing the support plate without any risk of collapse of the vertebral body.

According to a preferred form of construction of the invention, it is therefore provided that the limbs and the transverse web at their outer side remote from the load-bearing elements carry laterally outwardly projecting, plate-shaped supporting surfaces that form the external contour of the support plate. In other words, at the upper side of the support plate by providing laterally projecting supporting surfaces the cross section of the support plate is enlarged, the supporting surfaces in said case forming a part of the support plate and being preferably integrally connected to transverse web and limbs.

It is particularly advantageous when the two supporting surfaces associated with the limbs form mutually opposite outer lateral edges of the support plate, the distance between which increases from the ventral side to the dorsal side of the support plate. Thus, the area of the support plate is greater in the dorsal region than in the ventral region. In the dorsal region, the load-bearing capacity of the vertebral bodies is greater than in the ventral region, so that in the most stable region of the vertebral body a large support plate area is available, i.e. in said region the greatest portion of the force to be transmitted is taken up.

It may further be provided that the outer lateral edges of the support plate merge via arc-shaped portions into a ventral outer edge of the support plate that extends parallel to the transverse web. Thus, sharp edges that would increase the risk of collapse of the support plate are avoided.

It may further be provided that the outer lateral edges of the support plate likewise merge via arc-shaped portions into a dorsal outer edge of the support plate that extends parallel to the ventral outer edge. The overall result for the support plate is therefore a geometry that is of an approximately trapezoidal design and has rounded-off corners.

It may additionally be provided that the central region of the outer lateral edges is curved inwards. This inwardly curved portion of the outer lateral edges of the support plate is preferably of an arc-shaped design.

It is moreover advantageous when the inwardly curved portion of the outer lateral edges directly adjoins the arc-shaped portions of the outer lateral edges, via which arc-shaped portions said outer lateral edges merge into the ventral and dorsal outer edge of the support plate. On the one hand, these inward curves leave free regions of the end faces of the vertebral bodies that are less stable and therefore less capable of taking over the inertial forces and, on the other hand, these partial areas of the end faces of the vertebral bodies that are left free allow the accumulation of bony material and hence the formation of bone bridges between the adjacent vertebral bodies that are supported relative to one another by means of the vertebra replacement implant.

In a further preferred form of construction, it is provided that the supporting surface associated with the transverse web has in its central part an indentation that is open towards the outer edge. This indentation helps to reduce the cross-sectional area in the region of the transverse web and therefore promotes the elastic deformability of the transverse web in this region.

The supporting surfaces associated with the transverse web and the limbs preferably jointly surround a central opening that is open towards the dorsal outer edge.

This opening is preferably of a circular design.

This opening may be formed by the recess that is used to receive a bearing part or itself has the spherical contact surface, which rests against the spherical region of the bearing body.

It is advantageous when the central opening is open towards the dorsal outer edge via a radial slot, so that in this region the limbs may be pressed together, thereby allowing the support plate to be clamped to the bearing body.

In the dorsal outer edge of the support plate too, a central recessed portion may be disposed, which is preferably of a semi-circular design.

For fastening the support plates to the end faces of the vertebral bodies, protruding fixing projections may be provided, which are preferably disposed at the edge of the central opening. They are therefore situated in the region of the end face of the vertebral body that has a lower strength, so that these fixing projections upon positioning of the support plate against the vertebral body may easily penetrate into the vertebral body substance and therefore reliably secure the supporting surface against rotation and displacement.

The fixing projections may for example have the shape of thorns or points.

The fact that the points are disposed in the edge region of the central opening also prevents the fixing projections from damaging the vertebral body substance in regions of the end face of the vertebral body that have a high strength, with the result that these regions remain fully intact and are available undamaged for the purpose for load transmission.

In the supporting surfaces further holes may be provided, which are used for the passage of bony substance, i.e. bony substance may grow through these holes.

It is advantageous when lateral offsets are disposed in the edge of the central opening, these lateral recesses likewise increasing the flexibility of the support plate and promoting the ability of the support plate to be clamped onto the spherical bearing body.

Support plates of the described type may either be disposed on only one of the two load-bearing elements or they may easily be provided in the described manner on both load-bearing elements. In said case, it is possible to use support plates of different dimensions so that support plates adapted to the respective vertebra size may be provided at the upper side and at the underside of the vertebral body replacement implant. An exchange is easily possible even during an operation, should the surgeon deem this necessary.

The approximately butterfly-like shape of the support plate leads to particularly advantageous ratios of contact with a vertebral body. A support plate shaped in this manner is advantageously usable in a vertebral body replacement implant with a bearing arrangement on a spherical bearing body with a defined pivotal axis and a clamping device. It is however self-evident that the shape of this support plate may be used also in other vertebral body replacement implants, possibly also in intervertebral implants that are inserted into the spaces between two vertebral bodies and are to replace an intervertebral disk removed from this intervertebral space. The invention is therefore also directed to a correspondingly shaped support plate as such.

It is advantageous when the bearing shaft, in a support plate with bearing parts, passes through both the bearing part and an opening in the support plate. The bearing shaft then not only defines the pivotal axis of the structural unit of support plate and bearing part relative to the spherical bearing body, but the bearing shaft then also secures the support plate against a rotation relative to the bearing part about an axis perpendicular to the support plate.

It is advantageous when the clamping screw in its screw-in region is provided with a friction-reducing coating, for example with titanium oxide, thereby improving its screw-in properties.

It is further advantageous when the support plate is provided with a bone-friendly coating, for example with a microporous coating that promotes the growth of bony substance therein and hence the anchoring of the support plate on the vertebral body.

On the other hand, it may be advantageous to except the fixing projections of the support plate from the bone-friendly coating so that even after the operation these are still freely movable in the interior of the body and may adapt in an optimum manner to the vertebral body.

BRIEF DESCRIPTION OF THE DRAWINGS

The following description of preferred forms of construction of the invention serves in conjunction with the drawings to provide a detailed explanation. The drawings show.

DETAILED DESCRIPTION OF THE INVENTION

Figure 1:
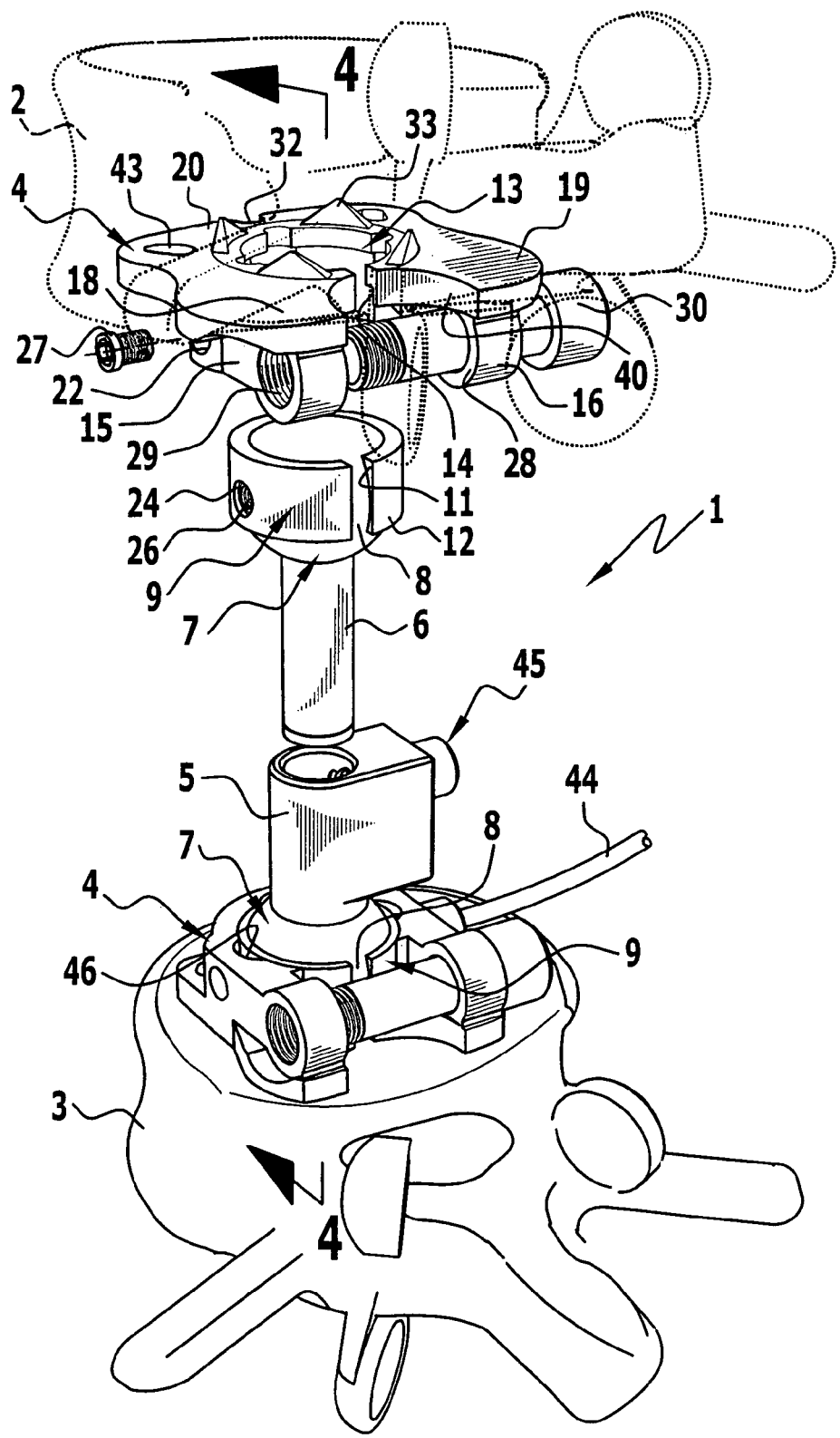
FIG. 1: a perspective exploded view of a vertebral body replacement implant between two vertebral bodies.
Figure 2:
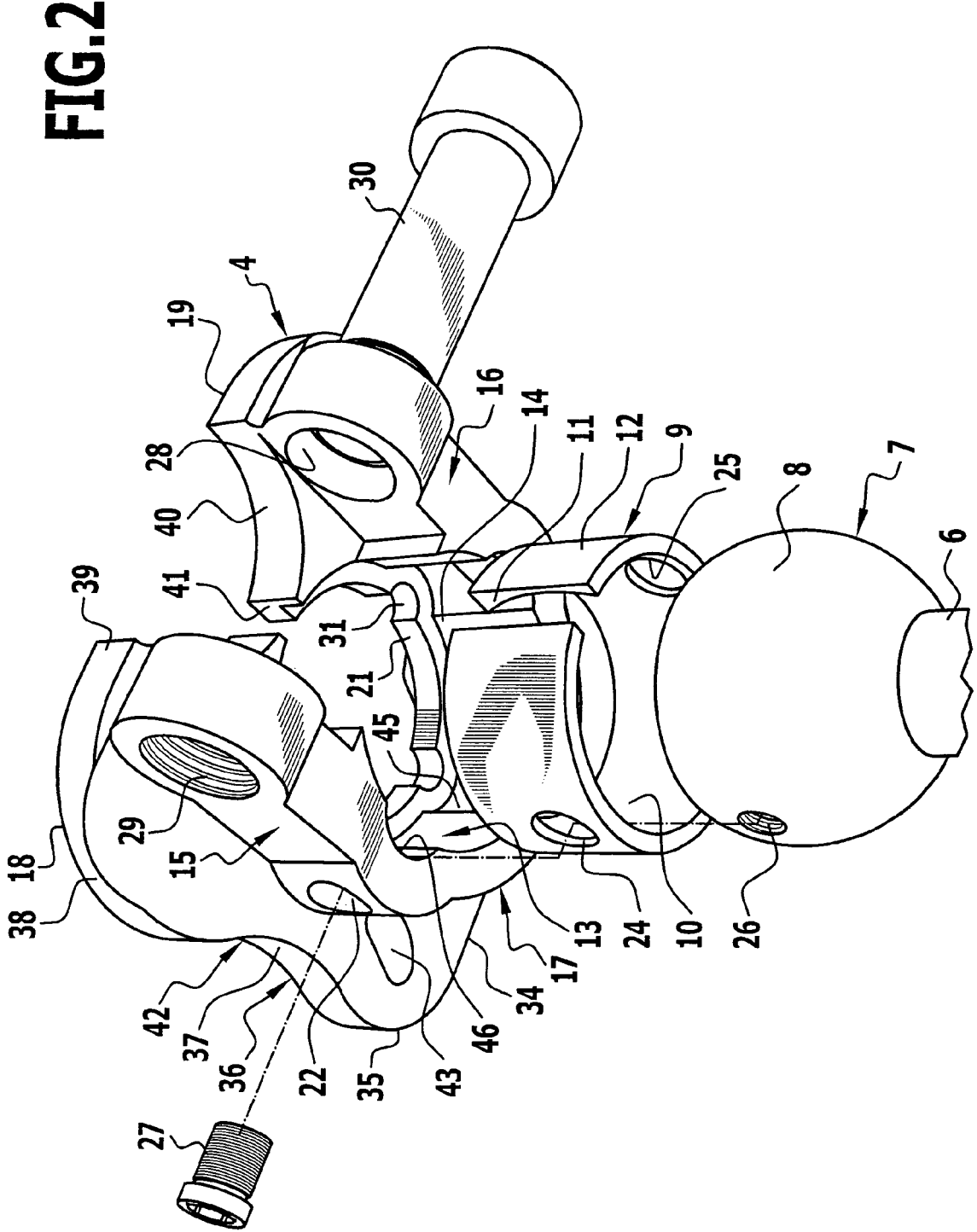
FIG. 2: an enlarged perspective view of the upper support plate of the vertebral body replacement implant of FIG. 1 viewed obliquely from below in the direction of the dorsal outer edge of the support plate.
Figure 3:
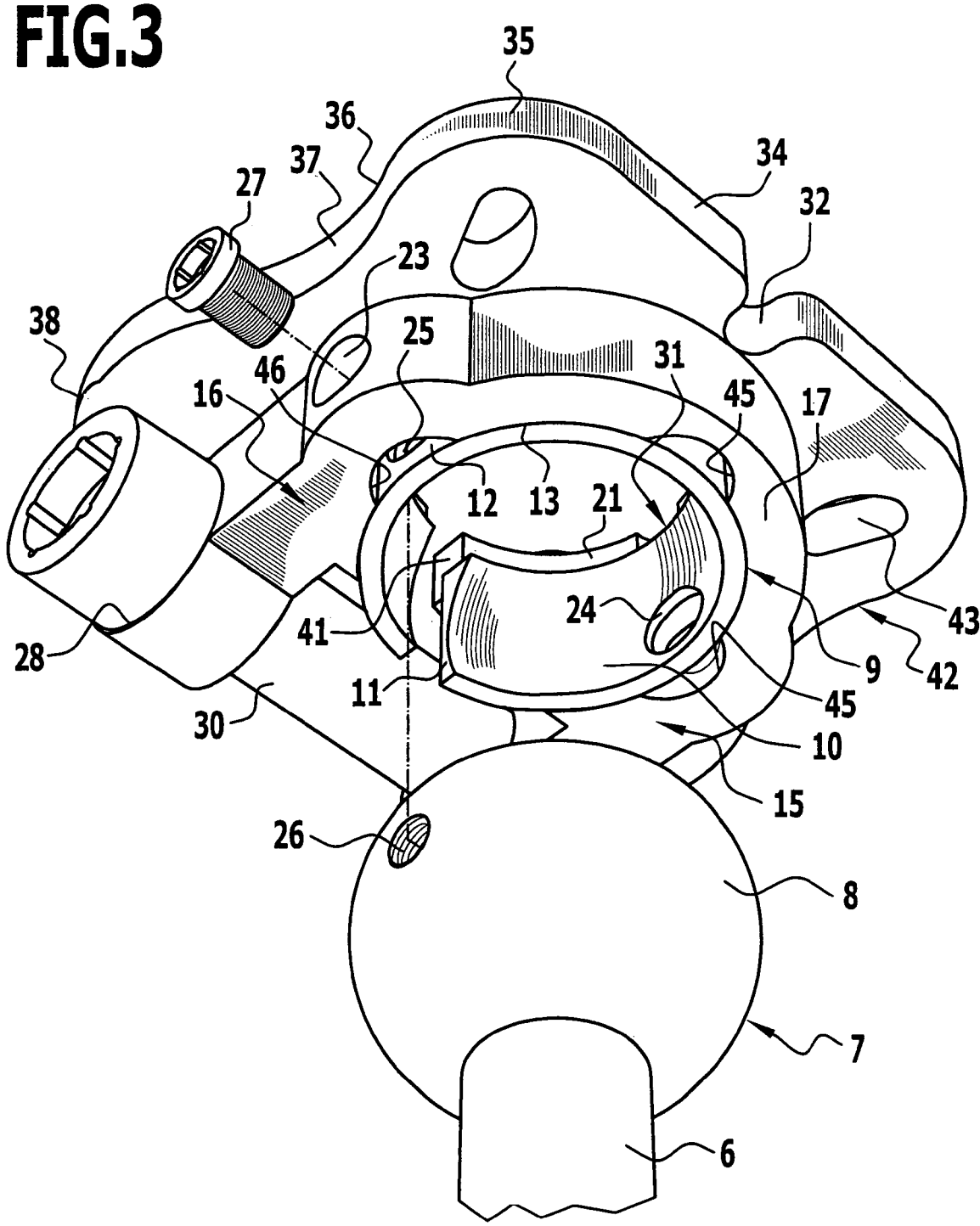
FIG. 3: a view similar to FIG. 2 in the direction of the ventral outer edge of the support plate with a bearing ring inserted into the support plate.
Figure 4:
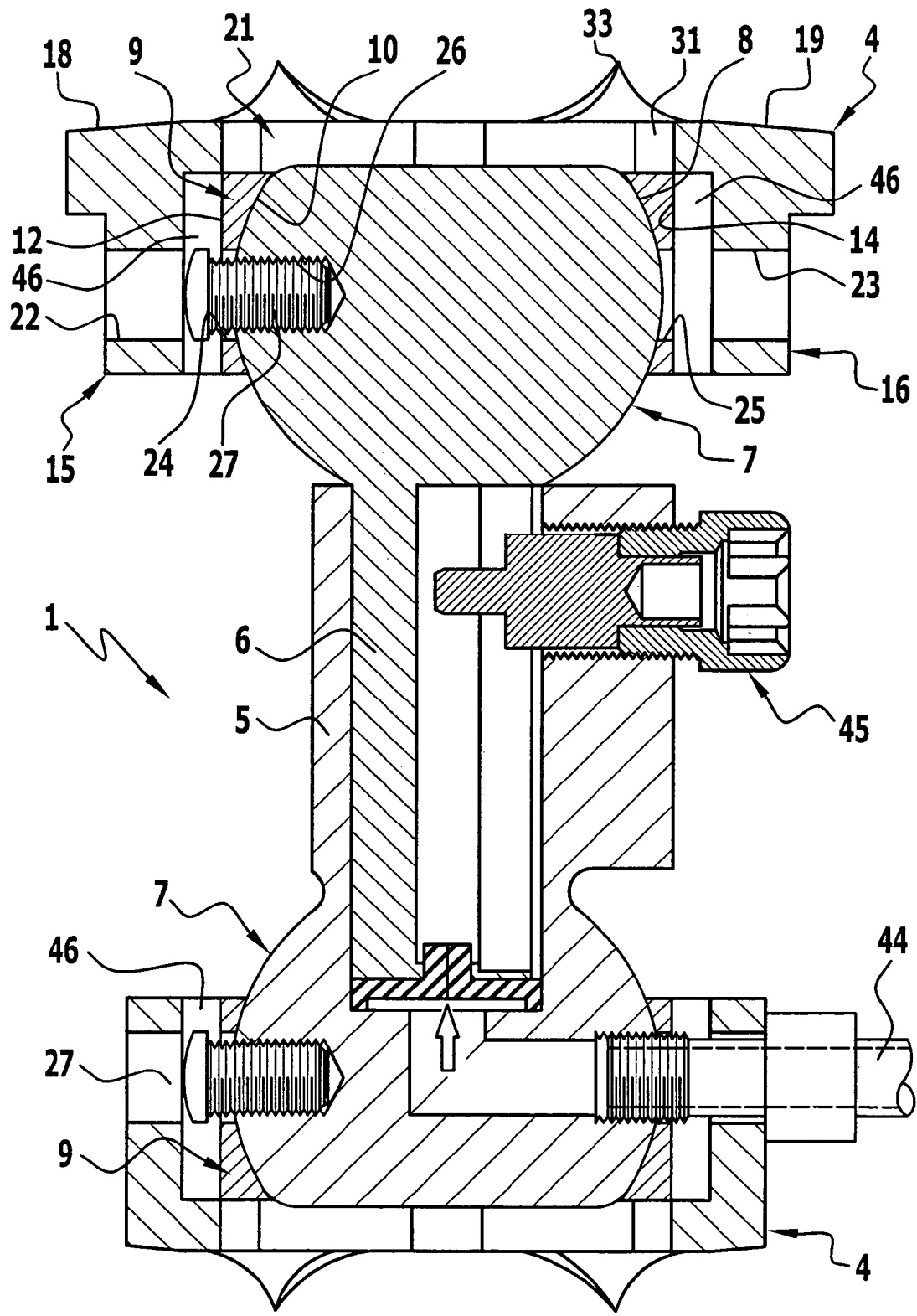
FIG. 4: a sectional view along line 4-4 in FIG. 1 of an assembled vertebral body replacement implant.
Figure 5:
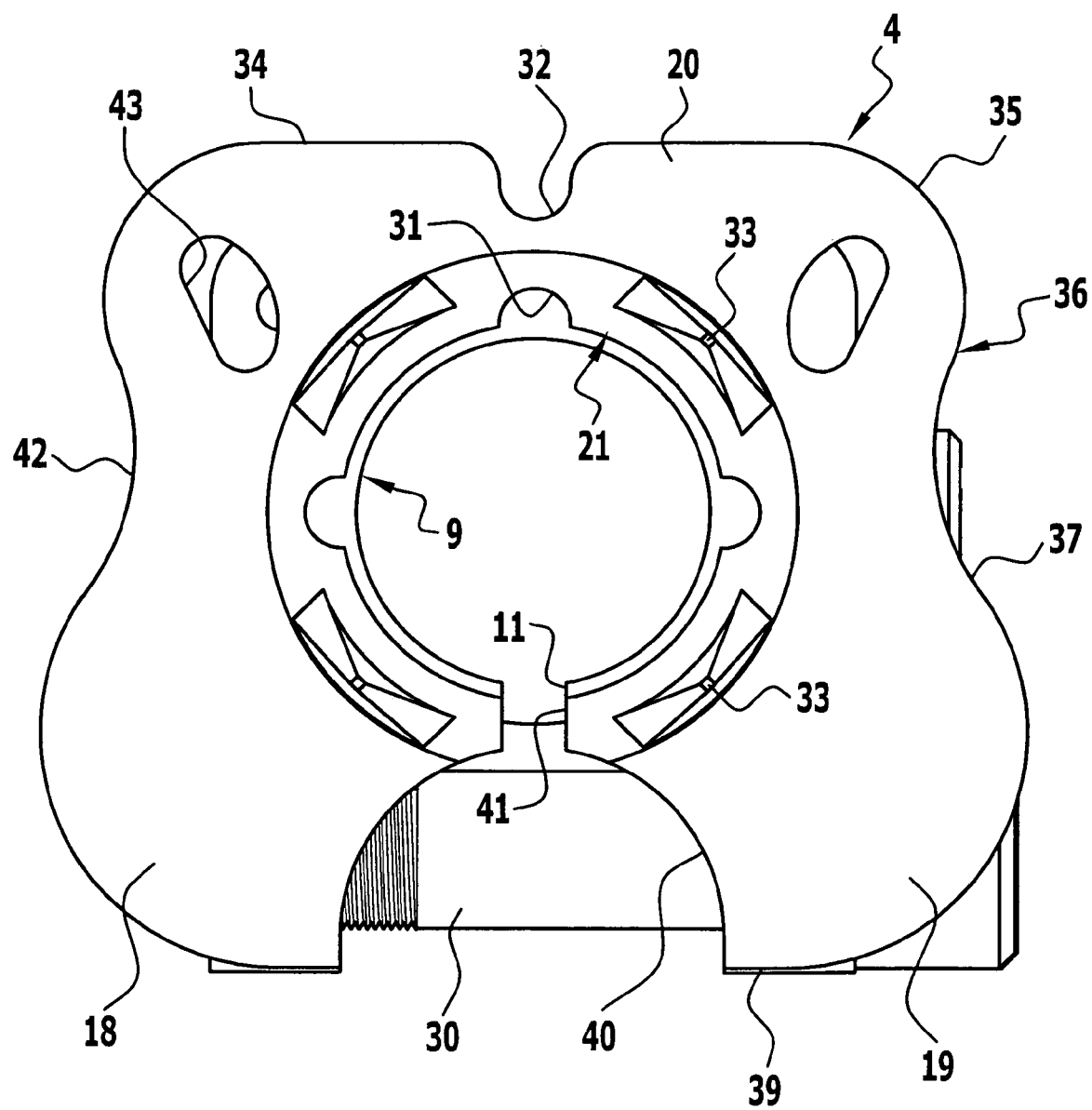
FIG. 5: a plan view of the support plate of the vertebral body replacement implant of FIGS. 1 to 4 and FIG. 6: a view similar to FIG. 3 in the case of a vertebral body replacement implant without a bearing ring disposed between support plate and load-bearing element.

The vertebral body replacement implant 1 illustrated in the drawings is to be inserted between two vertebral bodies 2, 3 that are not directly adjacent. Between these two vertebral bodies 2, 3 a vertebral body has been either completely removed or prepared in a manner not evident from the drawings so as to allow the vertebral body replacement implant 1 to be introduced into and passed through its interior, in other words so that the bridged vertebral body, whilst it is still there partially surrounding the vertebral body replacement implant, has been relieved of its load-bearing function.

The vertebral body replacement implant 1 has one support plate 4 each at its upper side and at its underside and, as these support plates are of an identical design, only one of the two support plates 4 is described in detail below.

Each of the two support plates 4 is connected to a load-bearing element, one of the two load-bearing elements being designed as a cylinder 5, the other as a piston 6 supported in a telescopically displaceable manner in the cylinder 5. The displacement may be effected in an as such known manner by filling the cylinder 5 with a hydraulic medium, the cylinder 5 together with the piston 6 therefore forming a piston-cylinder unit, by means of which the two parts are displaceable relative to one another. As a result of this displacement, the distance between the support plates 4 on the two ends of the vertebral body replacement implant 1 may be varied.

Both the cylinder 5 and the piston 6 on their ends remote from one another carry a bearing projection 7, which has a spherical or at least spherical-cap-shaped bearing surface 8 and is used for the pivotable mounting of the support plate 4, and as the bearing projection 7 on the cylinder 5 and on the piston 6 are of an identical design, the following description is limited to the description of the bearing arrangement of the upper support plate 4 on the piston 6.

In the embodiment of FIGS. 1 to 5, a bearing ring 9 is slipped from above onto the bearing projection 7 and has on its inner side a spherical contact surface 10, which is of a complementary design to the bearing surface 8 and lies with its surface against said bearing surface 8. The bearing ring 9 is subdivided at one point by a dividing slot 11 extending transversely of its peripheral direction, so that the bearing ring 9 may be bent elastically open and closed to a certain extent. Thus, by being elastically bent open it may be snapped onto the bearing projection 7 and, after snapping on, is held in this position by virtue of the spherical design of the bearing surface 8 and the contact surface 10.

The outer side 12 of the bearing ring 9, in contrast to the spherical contact surface 10, is of a cylindrical design and engages into a circular recess 13 in the underside of the support plate 4. The outer side 12 in said case rests against the cylindrical inner side 14 of this recess 13.

In a modified form of construction, it might also be provided that the outer side 12 of the bearing ring 9 is of a spherical-cap-like design and engages into a complementary recess in the underside of the support plate. Preferably, in said case there is not an extreme degree of crowning, i.e. the radii of the spherical surfaces are relatively large, so that the bearing ring only has to be expanded slightly in order to be slipped on over the bearing body. In the end position, the crowned outer side of the bearing ring then rests against the likewise crowned inner wall of the recess—after securing by clamping, the result is therefore a supporting in axial direction and hence a removal of load from the rotational bearing arrangement between bearing ring and bearing body.

The support plate 4 in its lower part facing the piston 6 has two limbs 15, 16 running parallel alongside and at a distance from one another and connected to one another by an approximately semi-circular transverse web 17, while disposed in the upper part facing the respective vertebral body are plate-shaped supporting surfaces 18, 19, 20, which project laterally beyond the limbs 15, 16 and the transverse web 17. These supporting surfaces are preferably integrally connected to the limbs 15, 16 and the transverse web 17. The two supporting surfaces 18 and 19 in said case each lie above and are associated with one of the limbs 15, 16, while the supporting surface 20 extends above and is associated with the transverse web 17.

The limbs 15, 16 and the transverse web 17, on the one hand, and the supporting surfaces 18, 19, 20 associated with them, on the other hand, jointly surround the circular recess 13 that passes right through the support plate 4 and is used to receive the bearing ring 9. However, the supporting surfaces 18, 19, 20 extend radially inwards into this recess 13 and therefore form an annular shoulder 21, which narrows the cross section of the recess 13 and as a stop limits the depth of insertion of the bearing ring 9 into the recess 13.

Situated in both limbs 15, 16, in the transition region to the semicircular transverse web 17, are mutually aligned bores 22, 23 that extend transversely of the longitudinal direction of the limbs 15, 16 and are bringable into alignment with corresponding bores 24, 25 in the bearing ring 9.

Incorporated in the spherical bearing projection 7 is a threaded bore 26, which extends transversely of the longitudinal direction of the piston 6 and in radial direction and into which a bearing screw 27 is insertable. This bearing screw 27 restricts the movement of the bearing ring 9 and hence of the support plate 4 relative to the spherical bearing projection 7, the movement namely being limited to a pivotal movement about the longitudinal axis of the bearing screw 27.

In the preferred embodiment, it is provided that each bearing projection 7 has only one threaded bore 26, so that a bearing screw 27 is inserted only into one side of the bearing projection 7, but by virtue of the symmetrical design of the support plate 4 with corresponding bores 22 and 23 on opposite sides and a corresponding design of the bearing ring 9 it is possible to connect the support plate 4 with the bearing ring 9 either at the upper side or at the underside of the vertebral body replacement implant 1 pivotably to a corresponding bearing projection 7 since, in the preferred embodiment, the threaded bores 26 of the bearing projections 7 at the upper side and the underside of the vertebral body replacement implant 1 are disposed at the same side.

By means of the bearing screw 27 the bearing ring 9 is connected in a defined and captive manner to the respective bearing projection 7. The support plate 4 may easily be exchanged, namely by removing it from the bearing ring 9 and optionally replacing it with another support plate. It is also possible, after removal of the support plate, for the bearing ring 9 to be removed from the bearing projection 7, the bearing ring merely having to be slightly elastically expanded for this purpose.

One of the two limbs 15, 16 carries on its free end a through-eye 28 extending parallel to the bores 22, 23, while the other limb carries an internally threaded through-bore 29 aligned with the through-eye 28. Into this internally threaded bore 29 there may be inserted a clamping screw 30, which is passed through the through-eye 28 and in the course of insertion clamps the free ends of the two limbs 15, 16 towards one another. In said case, these limbs are clamped with the inner side 14 of the recess 13 against the outer side 12 of the bearing ring 9, which is in turn compressed so that the bearing ring 9 is clamped with its contact surface 10 tightly against the bearing surface 8 of the bearing projection 7. This leads to a complete fixing of the structural part of support plate 4 and bearing ring 9 relative to the bearing projection 7, thereby cancelling the pivotability.

The limbs 15, 16 are in said case slightly elastically distorted, and for assisting this flexibility there are provided in the annular shoulder 21 a plurality of semicircular recesses 31, moreover in the supporting surface 20 associated with the transverse web 17 a central, substantially semicircular recess 32, and finally in the 9 transverse web 17 an, in cross section, semicircular recess 45 as well as in the limbs 15, 16 likewise, in cross section, semicircular recesses 46. These recesses lead to a weakening in this region and therefore increase the elastic deformability of the, as a whole, U-shaped support plate 4.

The annular shoulder 21 at its outer side carries a plurality of thorn-shaped fixing projections 33, which are therefore disposed directly on the edge of the central recess 13, while the remaining parts of the supporting surfaces 18, 19, 20 are free of such fixing projections.

The external contour of the support plate is determined by the external contour of the supporting surfaces 18, 19 and 20. The supporting surface 20, which is associated with the transverse web 17, has a straight ventral outer edge 34, which is interrupted only by the central recess 32 and which extends parallel to the longitudinal axis of the bearing screw 27. The outer edge 34 merges by means of a curved portion 35 into lateral outer edges 36 of the supporting surfaces 19 and 20. These lateral outer edges 36 are formed first by a part of the curved portion 35, then by an inwardly curved, arc-shaped portion 37, and finally by an outwardly curved portion 38, which terminates in a dorsal outer edge 39 that extends parallel to the ventral outer edge 34. Situated in the central part of the dorsal outer edge 39 is a semicircular offset 40, which communicates via a slot 41 with the recess 13, i.e. the recess 13 via this slot 41 is open in the direction of the offset 40. Thus, the curved portion 38 at its end turns at right angles into the offset 40.

The supporting surfaces 18, 19 and 20 therefore define a load-bearing surface that is narrower in the ventral part than in the dorsal part. In other words, the distance between the lateral outer edges 36 increases from the ventral side to the dorsal side, resulting as a whole in an approximately trapezoidal base with rounded-off outer edges and with arc-shaped indentations 42 at opposite sides. The end result is a butterfly-like external contour of this load-bearing surface. The load-bearing surface regions are so selected that they come to lie against the parts of the supporting surface of a vertebral body that is particularly capable of bearing load, so that the risk of collapse of the support plates 4 may be minimized.

Holes 43 are additionally provided in the supporting surfaces 18, 19 and 20 for the purpose of bone growth, so that in this region bony substance may grow through the supporting surfaces 18, 19 and 20.

Figure 6:
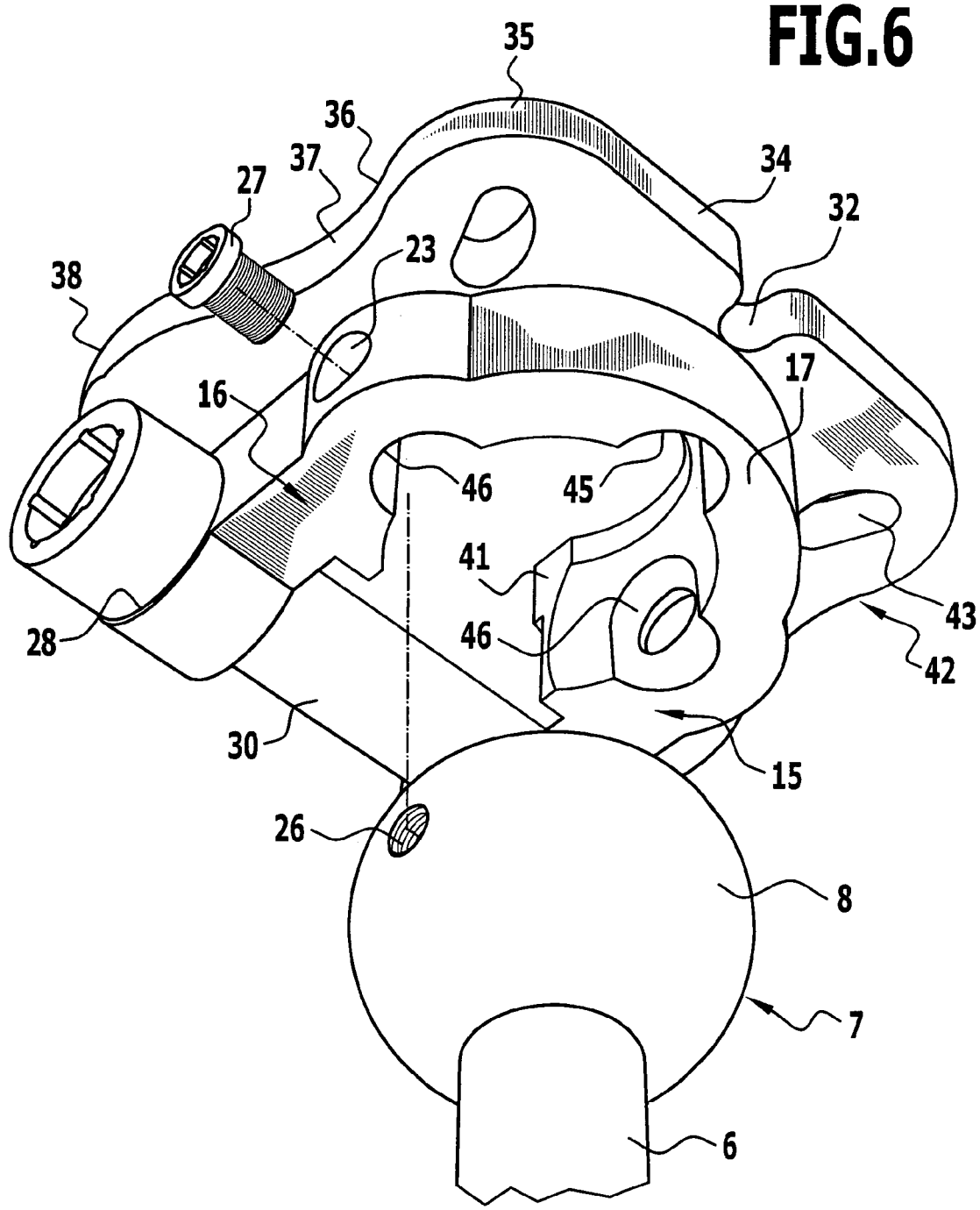

Whereas in the embodiment of FIGS. 1 to 4 the support plate 4 is mounted on the bearing projection 7 with a bearing ring 9 mounted therebetween, the embodiment of FIG. 6, which is otherwise of an identical construction to that of FIGS. 1 to 4 and in which identical parts therefore bear the same reference characters, dispenses with the bearing ring. Instead, in a similar manner to the bearing ring 9 at its contact surface 10, the inner side 14 of the recess 13 is of a spherical design and is adapted to the bearing surface 8 of the bearing projection 7, so that the support plate 4 lies with the inner side 14 directly against the bearing projection 7.

To insert the vertebral body replacement implant 1, it is pre-assembled outside of the body. For this purpose, the desired support plates 4 of the requisite geometries are placed, optionally with the interposition of the bearing ring 9, onto the bearing projection 7. In the pushed-together state, i.e. with the piston 6 pushed fully into the cylinder 5, the vertebral body replacement implant 1 is inserted into the space, where a vertebra is to be replaced or bridged, so that the support plates 4 are positioned opposite the vertebral bodies 2, 3 that are to be supported. In said case, the orientation is so selected that the pivotal axis defined by the bearing screw 27 extends in medial-lateral direction, the dorsal outer edges 39 in said case facing in dorsal direction, the ventral outer edges 34 in ventral direction.

In a form of construction without a bearing ring disposed between the support plate 4 and the bearing projection 7, the bearing screw 27 does not form a fully defined pivotal axis but projects with its head into the recesses 46 of the limbs and thereby limits the ability of the support plate to rotate relative to the bearing projection. Thus, in this form of construction too, there is substantially an ability of the support plate 4 to pivot relative to the bearing projection 7 about a bearing axis defined by the longitudinal axis of the bearing screw 27.

Through a connection line 44 a hydraulic medium, for example a saline solution, is then introduced in a manner not described in detail into the interior of the cylinder 5 so that the piston 6 is therefore pushed out of the cylinder 5. The support plates 4, which are freely pivotable about their pivotal axis, are then positioned against the vertebral bodies 2, 3 to be supported and adapt to the respective orientation of these vertebral bodies. As soon as the requisite spacing is achieved, the vertebral body replacement implant is fixed.

Fixing is effected firstly with regard to the spacing of piston 6 and cylinder 5, these two parts being clamped relative to one another by means of a clamping device 45 (not described in detail) so that they are no longer displaceable relative to one another.

Furthermore, the clamping screw 30 is inserted with a predetermined maximum torque into the internally threaded bore 29 and therefore clamps the two limbs 15, 16 against the bearing ring 9 or optionally directly against the bearing projection 7, thereby completely cancelling the ability of the support plate 4 to pivot relative to the bearing projection 7. By virtue of the spherical design of the bearing projection 7 and the bearing surface 8 of the bearing ring 9 or the inner side 14 of the recess 13 in a construction without a bearing ring, the bearing projection 7 is firmly enclosed at its circumference, thereby not only preventing pivoting but also effecting a fixing in axial direction. Load is therefore removed from the bearing screw 27, with a considerable portion of the axial forces and/or effective torques being taken up by this clamping by means of the clamping screw 30.

The end result is a secure fastening of the support plates 4 relative to the bearing projections 7 and of the two load-bearing elements, piston 6 and cylinder 5, with regard to the spacing of the two support plates 4. In this form, the vertebral body replacement implant 1 may remain in the body and perform the support function, it being optionally possible by embedding bony material to promote the growth of bone around the vertebral body replacement implant 1 so that a bone bridge may be produced between the vertebral bodies 2 and 3 supported by means of the vertebral body replacement implant 1.

The invention claimed is:

1. A vertebral body replacement implant comprising:
   an upper and a lower support plate for positioning against end faces of vertebral bodies;
   two load-bearing elements, the mutual spacing of the two load-bearing elements being adjustable;
   an articulated connection between at least one of the two load-bearing elements and a corresponding one of the upper and lower support plates, the load-bearing element in a region of the articulated connection to the corresponding support plate having a bearing projection with a spherical lateral support surface,
   one of the corresponding support plate or a bearing part connected to the support plate resting with a contact surface, which is of a complimentary design to the spherical lateral support surface, against the spherical lateral support surface of the bearing projection over an angular range that extends in a peripheral direction at least over 180°, the corresponding support plate or the bearing part being mounted on the bearing projection pivotably about a pivotal axis extending parallel to the support plate; and
   a clamping device that clamps the bearing projection, on the one hand, and the corresponding support plate or the bearing part in a contact region of at least one of the spherical lateral support surface and the contact surface, on the other hand, towards one another,
   wherein:
   the support plate is of a U-shaped design having two substantially parallel limbs connected by a transverse web;
   the limbs are disposed on either side of the spherical bearing projection,
   the pivotal axis extends parallel to the transverse web;
   the clamping device in a clamping position clamps the two limbs towards one another at their free ends remote from the transverse web; and
   in the clamping position the bearing projection and the support plate or the bearing part are clamped non-pivotably relative to one another and in a release position are released so that they are freely pivotable relative to one another about the pivotal axis.

2. Implant according to claim 1, wherein the clamping device is a clamping screw that extends parallel to the pivotal axis and rests against the free ends of the limbs.

3. Implant according to claim 2, wherein the longitudinal axis of the clamping screw and the pivotal axis define a bearing plane that extends at a spacing from, and substantially parallel to, a supporting surface of the support plate that is positionable against a vertebral body.

4. Implant according to claim 1, wherein the pivotal axis is defined by a bearing shaft that is adapted to be screwed into the bearing projection.

5. Implant according to claim 1, wherein the bearing part takes the form of a bearing ring that has a dividing slot extending transversely along its circumference.

6. Implant according to claim 5, wherein the bearing ring is disposed in a recess of the support plate and rests with its outer side against an inner wall of the recess.

7. Implant according to claim 6, wherein the recess forms a central opening in the support plate.

8. Implant according to claim 1, wherein the support plate in a region of the transverse web is of an elastically deformable design.

9. Implant according to claim 8, wherein the support plate has a lower thickness in the region of the transverse web than in a region of the limbs.

10. Implant according to claim 1, wherein the limbs and the transverse web on their outer side remote from the load-bearing elements carry laterally outwardly projecting; plate-shaped supporting surfaces that form an external contour of the support plate.

11. Implant according to claim 10, wherein the two supporting surfaces associated with the limbs form mutually opposite, outer lateral edges of the support plate, the spacing between which edges increases from a ventral side to a dorsal side of the support plate.

12. Implant according to claim 11, wherein the outer lateral edges of the support plate merge via arc-shaped portions into a ventral outer edge of the support plate that extends parallel to the transverse web.

13. Implant according to claim 11, wherein the lateral edges merge via arc-shaped portions into a dorsal outer edge of the support plate.

14. Implant according to claim 11, wherein a central region of the outer lateral edges is curved inwards.

15. Implant according to claim 14, wherein an inwardly curved region of the outer lateral edges of the support plate is of an arc-shaped design.

16. Implant according to claim 14, wherein an inwardly curved region of the outer lateral edges directly adjoins arc-shaped portions of the outer lateral edges, via which arc-shaped portions the outer lateral edges merge into ventral and dorsal outer edges of the support plate.

17. Implant according to claim 10, wherein the supporting surface associated with the transverse web has in its central part an indentation that is open in a direction of a ventral outer edge of the support plate.

18. Implant according to claim 10, wherein the supporting surfaces associated with the transverse web and the limbs jointly surround a central opening that is open in a direction of a dorsal outer edge of the support plate.

19. Implant according to claim 18, wherein the opening is of a circular design.

20. Implant according to claim 18, wherein the central opening via a radial slot is open in the direction of the dorsal outer edge.

21. Implant according to claim 10, wherein in a dorsal outer edge of the support plate a central, recessed portion is disposed.

22. Implant according to claim 21, wherein the recessed portion is of a semicircular design.

23. Implant according to claim 18, wherein at an edge of the central opening, outwardly projecting fixing projections are disposed.

24. Implant according to claim 23, wherein the fixing projections have a shape of thorns or points.

25. Implant according to claim 10, wherein holes are provided in the supporting surfaces.

26. Implant according to claim 18, wherein lateral recesses are disposed in an edge of the central opening.

27. Implant according to claim 1, wherein the articulated connection connects both load-bearing elements to a corresponding support plate.

28. Implant according to claim 4, wherein the bearing shaft, in a support plate with bearing parts, passes through both the bearing part and an opening in the support plate.

29. Implant according to claim 3, wherein the clamping screw in a screw-in region is coated with titanium oxide.

30. Implant according to claim 1, wherein the support plate is provided with a bone-friendly coating.

31. Implant according to claim 30, wherein fixing projections of the support plate are excepted from the bone-friendly coating.

* * * * *